(12) United States Patent
Sutton et al.

(10) Patent No.: US 7,816,554 B2
(45) Date of Patent: Oct. 19, 2010

(54) PROCESS FOR THE PRODUCTION OF ESTERS OF MONO-, DI- OR POLYCARBOXYLIC ACIDS

(75) Inventors: David M. Sutton, London (GB); Graham Reed, London (GB); Andrew G. Hiles, London (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 10/577,374

(22) PCT Filed: Oct. 18, 2004

(86) PCT No.: PCT/GB2004/004413

§ 371 (c)(1),
(2), (4) Date: Jan. 23, 2007

(87) PCT Pub. No.: WO2005/051885

PCT Pub. Date: Jun. 9, 2005

(65) Prior Publication Data

US 2007/0129565 A1    Jun. 7, 2007

(30) Foreign Application Priority Data

Oct. 31, 2003   (GB) ................. 0325530.4

(51) Int. Cl.
*C07C 67/00*   (2006.01)
(52) U.S. Cl. .................................... 560/204
(58) Field of Classification Search .............. None
See application file for complete search history.

(56) References Cited

U.S. PATENT DOCUMENTS

| | | | |
|---|---|---|---|
| 1,400,849 A | 12/1921 | Backhaus | |
| 2,551,625 A | 5/1951 | Morrell et al. | |
| 2,575,243 A | 11/1951 | Carlson et al. | |
| 2,587,753 A | 3/1952 | O'Connor et al. | |
| 2,610,206 A | 9/1952 | Highet at al. | |
| 2,638,481 A | 5/1953 | Nachod, Jr. | |
| 4,032,458 A | 6/1977 | Cooley et al. | |
| 4,058,555 A * | 11/1977 | Mims | 560/191 |
| 4,435,595 A | 3/1984 | Agreda et al. | |
| 4,584,419 A | 4/1986 | Sharif et al. | |
| 4,751,334 A | 6/1988 | Turner et al. | |
| 4,795,824 A | 1/1989 | Kippax et al. | |
| 5,008,046 A | 4/1991 | Bremus et al. | |
| 5,210,296 A * | 5/1993 | Cockrem et al. | 562/589 |
| 5,536,856 A | 7/1996 | Harrison et al. | |
| 5,719,311 A | 2/1998 | Wu et al. | |
| 6,045,703 A | 4/2000 | Miller | |
| 6,586,609 B2 | 7/2003 | Ruggieri et al. | |
| 6,815,525 B2 | 11/2004 | DeBruin | |
| 7,045,100 B2 | 5/2006 | Ergun et al. | |
| 2006/0252956 A1 | 11/2006 | Miller et al. | |

FOREIGN PATENT DOCUMENTS

| | | |
|---|---|---|
| DE | 32 22 837 A1 | 12/1983 |
| DE | 206 373 | 1/1984 |
| GB | 727 828 | 4/1955 |
| GB | 763 339 | 12/1956 |
| GB | 768 551 | 2/1957 |
| GB | 1 242 320 | 8/1971 |
| GB | 1 424 747 | 2/1976 |
| GB | 1 437 898 | 6/1976 |
| GB | 2 207 914 A | 2/1989 |
| WO | 88/00937 A1 | 2/1988 |
| WO | 90/08127 A1 | 7/1990 |
| WO | 93/00440 A1 | 1/1993 |
| WO | 97/43234 A1 | 11/1997 |
| WO | 97/43242 A1 | 11/1997 |
| WO | 9851657 A1 | 11/1998 |
| WO | 99/25678 A1 | 5/1999 |
| WO | 99/48852 A1 | 9/1999 |

OTHER PUBLICATIONS

International Search Report, PCT/GB2004/004413, dated Jan. 19, 2005, 4 pages.
Asthana, N., et al., "A Continuous Reactive Separation Process for Ethyl Lactate Formation," 2005, Organic Process Research & Development, 9(5):599-607 (Abstract).
Bock, et al., "Design and Control of a Reaction Distillation Column Including the Recovery System," 1997, Chem. Eng. and Proc. ,36(2):101-109 (Abstract).
Deng, et al., "Synthesis of Tributly Citrate Catalyzed by Sodium Hydrogen Sulfate," 2005, J Shangqiu Teachers College, 21(2):113-115 (Abstract).
Gangadwala, J., et al., "Esterification of Acetic Acid with Butanol in the Presence of Ion-Exchange Resins as Catalysts," 2003, Ind. Eng. Chem. Res., 42(10)2146-2155 (Abstract).
Gotze, L., et al., "Reactive Distillation with KATAPAK," 2001, Catalysis Today, 69(1-4):201-208 (Abstract).
Hanika, J., et al., "Butylacetate Via Reactive Distillation—Modelling and Experiment," 1999, Chemical Engineering Science, 54(21):5205-5209 (Abstract).
Hiwale, R.S., et al., "Industrial Applications of Reactive Distillation: Recent Trends," 2004, Int. J. Chem. React. Eng., 2(R1):54 pages.
Kolodziej, et al., "Mass Transfer of Hydraulics for KATAPAK-S," 2004, Chem. Eng. Proc., 43(3):457-464 (Abstract).
Liu, et al., "Catalytic Synthesis of Tri-butyl Citrate with Dealumiinated USY," 2003, Chinese Journal of Synthetic Chemistry, 11(2):175-177 (Abstract).
Mahajani, S.M., et al., "Reactive Distillation: Process of Commercial Importance," 2000, Encyclopedia of Separation Science, Wilson, (Continued)

*Primary Examiner*—Daniel M Sullivan
*Assistant Examiner*—Yevegeny Valenrod
(74) *Attorney, Agent, or Firm*—Senniger Powers LLP

(57) ABSTRACT

A process for the production of carboxylic acid esters by reaction of a carboxylic acid selected from mono-, di- and polycarboxylic acids, with an alcohol in the presence of water of solution comprising the steps of: (a) providing a solution comprising the carboxylic acid and the water of solution; (b) reacting the solution of the carboxylic acid in an esterification zone with an alcohol to form an ester and water of esterification; (c) removing the water of solution and the water of esterification; and (d) recovering the ester.

19 Claims, 3 Drawing Sheets

OTHER PUBLICATIONS

Edlard, Poole C.A. and m. Cooke, Eds. 3:4075-4082.

Moritz, P., et al., "Fluid Dynamics in Reactive Distillation Packing Katapak -S," 1999, Chemcial Engineering Science, 54:1367-1374.

Nong, L., et al., "Synthesis of Tributyl Citrate with Aluminum Phosphotungstate Supported on Activated Carbon," 2004, Jingxi Huagong Zhongjianti, 32(3):50-52, 54 (Abstract).

Omota, F., et al., "Fatty Acid Esterification by Reactive Distillation. Part 1: Equilibrium-Based Design," 2003, Chemical Engineering Science, 58:3159-3174.

Ratheesh, S., "Holdup and Pressure Drop Studies in Structured Packings with Catalysts," 2004, Chemical Engineering Journal, 104:45-54.

Schmitt, et al., "Synthesis of N-Hexyl Acetate by Reactive Distillation," 2004, Chem. Eng. Proc., 43:397-409.

Schmitt, et al., "N-Hexyl Acetate Pilot Plant Reactive Distillation with Modified Internals," 2005, Chem. Eng. Proc., 44:677-685 (Abstract).

Sharma, M.M., et al., "Chapter 1. Industrial Application of Reactive Distillation in Reactive Distillation," 2003, Reactive Distillation: Status and Future Directions, pp. 3-29, Sundmacher and Kienle, Eds., Wiley-VCH Berlag GmbH & Co. KGaA, Germany.

Shi, et al., "The Synthesis of Tributyl Citrate Catalyzed by Solid Super Acid S2O82-/TiO2-SiO2," 2004, Applied Chemical Industry, 33(3):41-43 (Abstract).

Smejkal, Q., et al., "2-Methylpropylacetate Synthesis in a System of Equilibrium Reactor and Reactive Distillation Column," 2001, Chemical Engineering Science, 56:365-370.

Spes, H., "Catalytic Reactions in Ion-Exchange Columns Under Conditions of The Chemical Equilibrium Shift," 1966, Chemiker-Ztg./Chem Apparatur, 90(13):443-446.

Stankiewicz, et al., "Process Intensificaton: Transforming Chemical Engineering," 2000, Chemical Engineering Progress, 22-34.

Tao, X., et al.,1998, Huaxue Shijie, 39(6):302-304.

Taylor, R., et al., "Chapter 9. Modeling of Homogeneous and Heterogeneous Reactive Distrillation Processes," 2003, Reactive Distillation, pp. 217-240, sudmacher and Kienle, Eds., Wiley-VCH Berlag GmbH & Co. KGaA, Germany.

Taylor, R., et al., "Modelling Reactive Distillation," 2000, Chemical Engineering Science, 55:5183-5229.

Van Baten, J.M., et al., "Liquid-Phase Mass Transfer Within KATAPAK-S Structures Studied Using Computational Fluid Dynamics Simulations," 2001, Catalysis Today, 69:371-377.

Zheng, et al., "Study on the Synethesis of Tributyl Citrate," 2004, Fine Chemical Intermediates, 34(1):28-30 (Abstract).

Asthana, N., et al., "A Continuous Reactive Separation Process for Ethyl Lactate Formation," 2005, Organic Process Research & Development, 9(5):599-607.

Bock, et al., "Design and Control of a Reaction Distillation Column Including the Recovery System," 1997, Chem. Eng. and Proc. ,36(2):101-109.

Gangadwala, J., et al., "Esterification of Acetic Acid with Butanol in the Presence of Ion-Exchange Resins as Catalysts," 2003, Ind. Eng. Chem. Res., 42(10)2146-2155.

Gotze, L., et al., "Reactive Distillation with KATAPAK," 2001, Catalysis Today, 69(1-4):201-208.

Hanika, J., et al., "Butylacetate Via Reactive Distillation—Modelling and Experiment," 1999, Chemical Engineering Science, 54(21):5205-5209.

Kolodziej, et al., "Mass Transfer and Hydraulics for KATAPAK-S," 2004, Chem Eng and Proc, 43:457-464.

Schmitt, et al., "n-Hexyl Acetate Pilot Plant Reactive Distillation with Modified Internals," 2005, Chem Eng and Proc, 44:677-685.

Schmitt, et al., "Synthesis of n-Hexyl Acetate by Reactive Distillation," 2004, Chem Eng and Proc, 43:397-409.

Nong, "The Synthesis of Tributyl Citrate by Aluminium Phosphotungstate Supported on Activated Carbon," 2004, Fine Chem Intermed, 35(3):50-54, Non English Document with English Abstract.

* cited by examiner

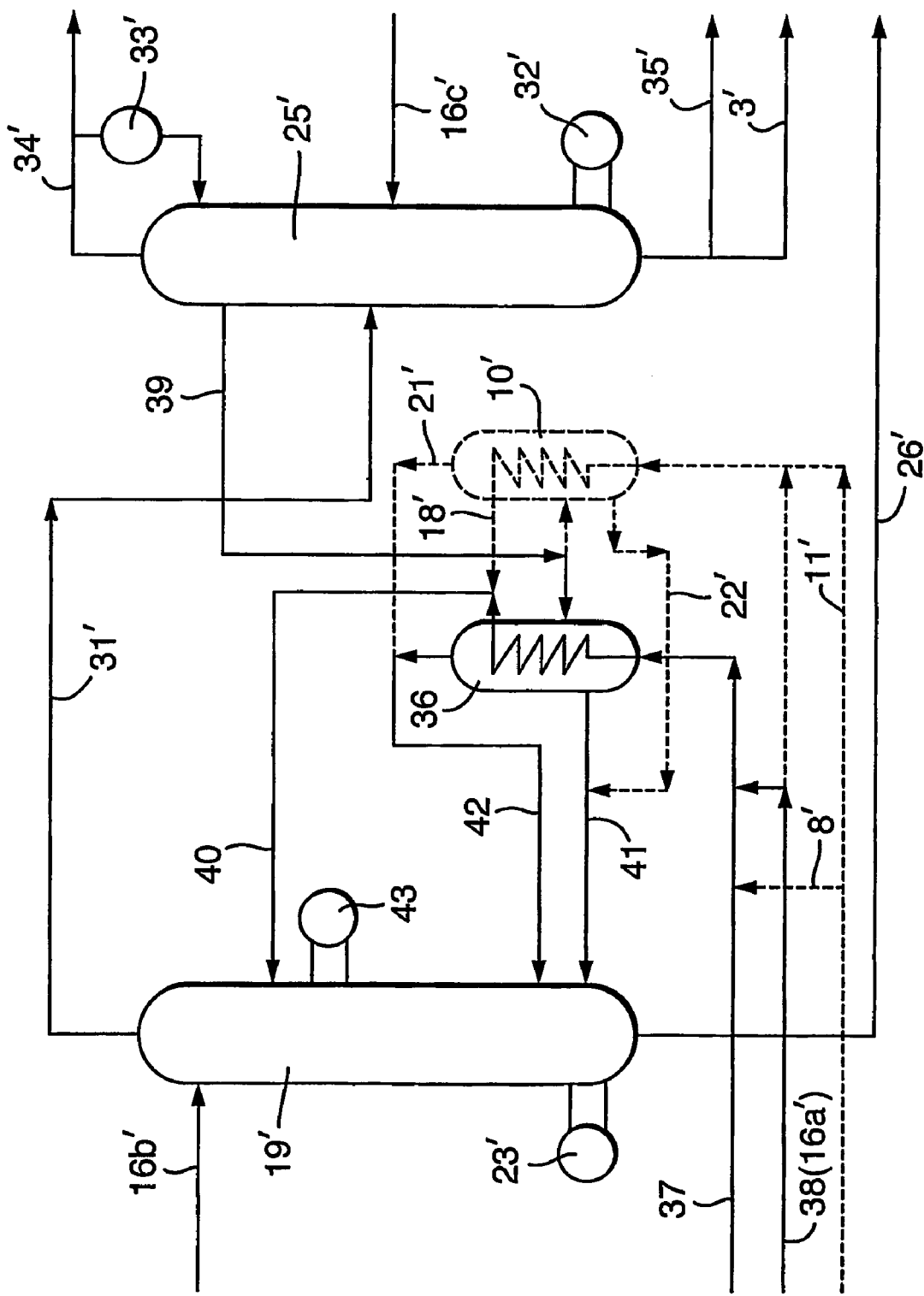

PROCESS FOR THE PRODUCTION OF ESTERS OF MONO-, DI- OR POLYCARBOXYLIC ACIDS

The present invention relates to a process for the esterification of carboxylic acids in the presence of water. In particular, it relates to a process for the esterification of maleic acid, succinic acid or 3-hydroxypropionic acid in a water wet stream.

It is well known that the production of an ester may be achieved by reacting a carboxylic acid with an alcohol in an acid catalysed reversible reaction in which water is formed as a by-product. It is normally necessary to remove the so-called "water of esterification" to drive the equilibrium in favour of the ester. Further, since the presence of water will drive the equilibrium away from ester formation, any water present must be removed before esterification is completed.

Esters have a wide number of uses in industry. A major use of the diester of maleic acid and succinic acid is in the production of one or more of butane-1,4-diol, tetrahydrofuran and/or γ-butyrolactone. The ester of 3-hydroxypropionic acid may also be a useful starting material in the production of propane-1,3-diol.

Butane-1,4-diol has conventionally been produced from a refined maleic anhydride feedstock, which is esterified to di-ethyl maleate or di-methyl maleate, conveniently in a two stage process, and then subsequently subjected to hydrogenolysis to produce a mixture of butane-1,4-diol, tetrahydrofuran and γ-butyrolactone. Examples of processes utilising maleic anhydride in the production of these products are described in detail in WO-A-99/48852, WO-A-97/43234, WO-A-97/43242, U.S. Pat. No. 4,795,824 and in WO-A-90/08127, which are incorporated herein by reference. The hydrogenation of dialkyl maleates to yield butane-1,4-diol is discussed in detail in U.S. Pat. No. 4,584,419, U.S. Pat. No. 4,751,334 and WO-A-88/00937, which are also incorporated herein by reference.

The maleic anhydride is normally produced by vapour phase oxidation of a hydrocarbon feedstock, normally benzene, or n-butane, in the presence of a partial oxidation catalyst. Whichever process conditions are used, the maleic anhydride present in the resultant hot vaporous reaction stream will include nitrogen, maleic anhydride, water, carbon oxides, oxygen, unreacted feedstock, light impurities (for example acetic and acrylic acids) and inert gases. In order to recover the maleic anhydride, this hot stream may be cooled to condense some of the maleic anhydride present. The remaining maleic anhydride product, or if the condensing step is omitted all of the maleic anhydride product, is then recovered via either an aqueous or a solvent based absorption system.

With an aqueous recovery system, the cooled gases are fed to an aqueous absorber unit and maleic anhydride is scrubbed from the gases as an aqueous solution of maleic acid. Scrubbing with water is described in detail in, for example, U.S. Pat. No. 2,638,481 which is incorporated herein by reference. The aqueous solution of maleic acid must then be dehydrated to remove the water and to convert the maleic acid back to maleic anhydride.

One method utilised for the dehydration of the maleic acid to the anhydride is azeotropic distillation in which the acid solution is converted into the anhydride using an azeotropic agent such as xylene. The dehydrated product must then be distilled to give product grade maleic anhydride. Examples of this process can be found in GB-A-727828, GB-A-763339, GB-768551, GB-A-1242320 and GB-A-1424747 which are incorporated herein by reference.

In one alternative arrangement the maleic acid solution is concentrated by evaporation and is then thermally heated to form the maleic anhydride. This crude maleic anhydride must then be refined to give a product grade stream.

The inclusion in the plant of the equipment required for the isolation of product grade maleic anhydride adds significantly to the cost of production. Where the maleic anhydride is then used in the production of butane-1,4-diol, tetrahydrofuran and/or γ-butyrolactone there will be a consequential impact on the production costs of these products.

A further problem associated with the production of maleic anhydride particularly where an aqueous recovery step is utilised is that fumaric acid is normally formed. The presence of this isomerisation by-product is disadvantageous in part as it represents a loss of valuable maleic anhydride. However, more seriously fumaric acid has a melting point of 287° C. which is substantially above that of maleic anhydride which is 52.85° C. As a result there is a tendency for deposits of solid fumaric acid to build up on, for example, heat exchanger surfaces. These deposits must be periodically removed which necessitates the shut-down of the plant. Typically, removal of the deposits is carried out by the use of water and/or sodium hydroxide solution to give an aqueous solution which will require effluent treatment.

Any malic acid present as a by-product is also disadvantageous since if it is present with maleic anhydride in the starting material for a butane-1,4-diol plant it may result in the formation of the butane-1,2-diol. Further, if the malic acid is present at a high concentration, inhibition of the catalyst may be noted.

Succinic acid which may also be esterified, for example, for use as a starting material for the production of butane-1,4-diol, tetrahydrofuran and/or γ-butyrolactone and 3-hydroxypropionic acid which may be esterified for use in the production of propanediol, are generally produced by fermentation. Such processes result in products which are contained in a substantial excess of water. Again, it is generally required that this water be removed before the acid is subjected to esterification. The dehydration procedure is costly and may result in the formation of undesirable by-products.

In order to overcome the problems associated with the presence of maleic acid and fumaric acid, GB 2207914, which is incorporated herein by reference discloses a process in which a hydrocarbon feedstock is converted to maleic anhydride and an acidic residue comprising a mixture of maleic acid and fumaric acid. The residue is reacted with an alcohol to form a diester in either a one or two stage process. The water of esterification is driven off in the, or the final, esterification column. Whilst this process goes some way to addressing the problems associated with fumaric acid formation, the treatment of the residue stream adds to the overall cost of the process.

An alternative esterification process is described in WO90/08127 in which a monoesterified carboxylic acid is passed downwardly through a reactor containing a plurality of esterification trays and is treated with relatively dry alcohol vapour which assists the water of esterification to be driven off.

Whilst these process provide means for removing the water of esterification to drive the reaction towards completion, they do not contemplate the possibility of the esterification being carried out in the presence of a high level of water of solution.

It is therefore desirable to provide an improved esterification process which can successfully take place in the presence of water of solution.

Thus according to a first aspect of the present invention there is provided a process for the production of carboxylic acid esters by reaction of a carboxylic acid selected from mono-, di- and polycarboxylic acids, with an alcohol in the presence of water of solution comprising the steps of:

(a) providing a solution comprising the carboxylic acid and the water of solution;

(b) reacting the solution of the carboxylic acid in an esterification zone with an alcohol to form an ester and water of esterification;

(c) removing the water of solution and the water of esterification; and (d) recovering the ester.

The process of the present invention is preferably a continuous process.

Thus the present invention provides a process in which the esterification can be carried out in the presence of a substantial excess of water such that some or all of the problems set out above are minimised or obviated.

The present invention is suitable for use in the esterification of a large range of carboxylic acids. The esterification may be a mono-, di- or polyesterification. Examples of monoesterification reactions include the production of alkyl esters of aliphatic monocarboxylic acids from an alcohol and a monocarboxylic acid. The monocarboxylic acid may be of any suitable chain length and may be straight chain or branched, saturated or unsaturated. Examples of monocarboxylic acids include those having from $C_3$ to $C_{18}$.

Another class of carboxylic acid esters which can be produced by the process of the present invention are dialkyl esters of aliphatic and cycloaliphatic $C_4$ to $C_{18}$ saturated or unsaturated, straight chain or branched, dicarboxylic acids. Examples of esters falling within this category include diallyl oxalates, dialkyl maleates, dialkyl succinates, dialkyl fumarates, dialkyl glutarates, diallyl pimelates, dialkyl axelates and the like.

Aromatic carboxylic acid esters may also be produced by the process of the present invention.

Examples of polyalkyl esters which can be produced in accordance with the present invention include alkyl esters of citric acid.

Alkyl esters derived from reacting the acids with alcohols containing from 1 to about 10 carbon atoms are of especial importance, with those being derived from methanol, ethanol, propanol and butanol being of particular interest. Diols may also be used.

The present invention is particularly suitable for application to the production of di-($C_1$ to $C_4$ allyl) maleate, di-($C_1$ to $C_4$ alkyl) succinate and a $C_1$ to $C_4$ alkyl ester of 3-hydroxypropionic acid.

In a most preferred arrangement of the present invention, the process relates to the formation of di-($C_1$ to $C_4$ alkyl) maleate and thus the carboxylic acid provided in step (a) will be maleic acid. The maleic acid will normally be produced by vapour phase oxidation of a hydrocarbon feedstock, normally benzene or n-butane in the presence of a partial oxidation catalyst, such as vanadium pentoxide, by conventional means. The resultant vapour stream from the oxidation reactor containing maleic anhydride can be recovered as maleic acid by contact with water or partially condensed as maleic anhydride or by a combination of partial condensing and contact with water. In addition to cooling the vapour stream, the water will also convert the maleic anhydride to maleic acid. Since an aqueous solution of maleic acid is suitable for use as the feed of the present invention, the requirement for the expensive evaporation and dehydration steps and the scrubbers for the recovery of maleic acid from vent streams of the prior art systems are obviated. The steps for recovering maleic acid from vent streams are combined with the esterification units and maleic acid is recycled with the water stream to the absorber. By this means essentially all of the maleic acid is converted to ester, and a small amount recycled with minor losses. For example losses in the order of 0.5% may be achieved.

Further, the problems described above relating to the formation of fumaric acid are obviated. Although fumaric acid will still be formed in the production and recovery of maleic anhydride, as an aqueous solution is used the problems associated with high fumaric formation leading to crystalline deposits of fumaric acid associated with prior art processes are minimised. Further, although low levels of fumaric acid may be present in the feed, it will form an ester in the esterification zone and, if processed further such as by hydrogenation will yield the desired products of the reaction. Thus there is no requirement to remove the fumaric acid from the feed.

Thus in one arrangement of the present invention, the carboxylic acid is maleic acid which is formed by hydrolysis of the product from a maleic anhydride reactor and the water of solution and the water of esterification may be recycled to the absorber in which hydrolysis of the product from the maleic anhydride reactor is carried out.

The feed to step (a) may comprise from about 20 to about 100% of an aqueous solution of the acid. The acid feed may be processed prior to being introduced in step (a) to reduce the water content, and/or to reduce or remove trace contaminants such as phosphorous or metals.

The formation of diesters will normally occur in a two-stage process. This can be exemplified by reference to the esterification of maleic acid. First the maleic acid is reacted with an alcohol, such as methanol or ethanol, to form the corresponding monoalkylmaleate. This is subsequently converted to the corresponding dialkylmaleate.

The first part of the reaction is illustrated in Scheme 1:

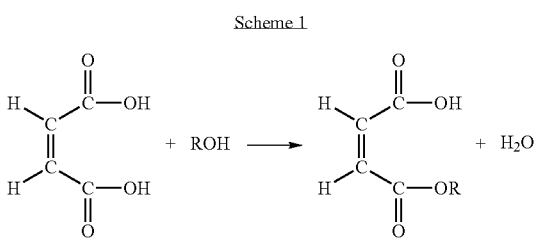

where R is an alkyl radical.

The mono-alkyl maleate then reacts with further alcohol to form the diester. The reaction concerned is illustrated in Scheme 2:

Scheme 2

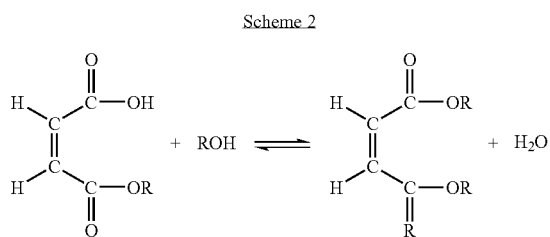

where R is as defined above.

In a procedure in which maleic acid is used as the feed if, for example, methanol is used to produce di-methyl maleate, two moles of methanol are required per mole of maleic anhydride and one mole of reaction water is produced in the esterification reaction. The two principle reactions occur essentially in series and are described in Schemes 3a and 3b. Scheme 3 describes the overall reaction.

Scheme 3a

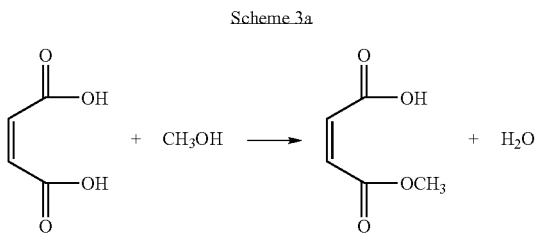

Scheme 3b

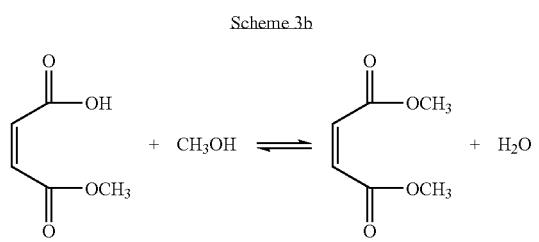

Scheme 3

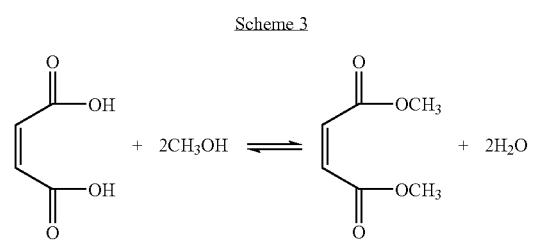

The extent of reaction in the second esterification step illustrated in Scheme 3b is limited by chemical equilibria and it is therefore necessary to remove the water produced (known as the water of esterification) to enable the reaction to go largely to completion. The water may be removed by any suitable means but will usually be removed in a column reactor. It will be necessary to use a significant amount of excess methanol (commonly about 2 to about 5 moles in total per mole of maleic anhydride feed) to strip out the water of esterification. As the rate at which it is necessary to circulate the methanol determines the diameter of the reaction column and significantly effects the heat input requirement of the esterification process, there is a strong economic incentive to minimise the methanol circulation rate within the esterification reaction column but this in turn can minimise the ability to remove the water. Similar problems are noted with other esterification reactions.

As illustrated in Schemes 1 and 2, with a feedstock comprising a maleic acid solution, two moles of water are released by the overall reaction to the dimethyl maleate. Further since the maleic acid feed is in an aqueous solution, additional water is added to the system. Indeed where the maleic acid feed is provided directly by scrubbing vaporous maleic anhydride in water, water may constitute a large fraction of the feed, typically 50-70 wt %.

There are certain disadvantages associated with having a high water content. For example, it will be understood that in a 50 wt % maleic acid aqueous solution there are 6.4 moles of water of solution for each mole of maleic acid and therefore the total quantity of water to be removed would increase by 7.4 moles/mole of maleic acid over the single mole that is required to be removed from a reaction having a maleic anhydride feed. Even if the feed comprised a 95 weight % maleic acid solution, 1.3 moles of water per mole of maleic acid would have to be removed above the single mole which has to be removed in the reaction utilising a conventional maleic anhydride feed.

A further problem associated with having a high water content in the reactor is that it may be difficult to maintain temperatures in the reaction vessel at a sufficiently high level which may reduce the reaction rates.

However, the process of the present invention allows an aqueous feed to be utilised.

In one arrangement of the present invention, the water removed in step (c) may be recycled to step (a).

Various process steps may be incorporated into the process of the present invention which will enable significant quantities of water to be removed from the esterification zone such that a carboxylic acid with free water of solution may be economically used as the feedstock.

In one arrangement of the present invention to assist in the removal of the water, one or more heaters may be provided in the esterification zone. In one preferred arrangement the heater may be located in the reactor, which may be a catalytic reaction column, close to the feed point. The heater will increase the heat of the feed and assist in driving some of the water content of the feed up the reactor or column. By this means the high water content of the feed will have a reduced impact on the overall water content and temperature of areas of the reactor, which may include reaction trays located in the column below the level of the heater.

Where the esterification reaction is a di-esterification, the two step esterification reaction may occur in a single reactor which may be a stirred tank reactor or a column reactor, in separate zones within the single reactor or in separate reactors which may be selected from stirred tank reactors or column reactors. In a preferred arrangement, the reactions are carried out in separate reactors with at least the second step being carried out in a column reactor. A plug flow reactor may also be used and is particularly suitable for the first step.

Where the esterification zone comprises at least two separate reactors, or two zones within a single reactor, the first being for the mono-esterification reaction and the second for the reaction of the mono-ester to form the diester, a heater may be provided in one or both reactors or areas of the reactor.

The heater will advantageously be located in the second reactor or second section of the reactor, i.e. that in which the mono-ester is reacted with the alcohol to form the diester.

Additionally or alternatively, the reactor in which the mono-ester is formed may include means for stripping out the water so that the product mono-ester stream has a low free water content which is preferably less than about 30 mole percent.

A catalyst may be required in one or both stages of the esterification. It is likely that the second stage will have to be carried out in the presence of a catalyst. The catalytic esterification zone may comprise a plurality of stirred tank reactors, as disclosed in U.S. Pat. No. 4,795,824, but preferably comprises a column reactor of the type disclosed in WO-A-90/08127, which is incorporated herein by reference.

The column reactor will contain a plurality of esterification trays each having a predetermined liquid hold up and containing a charge of a solid esterification catalyst. Each tray has a vapour upcomer means to permit vapour to enter the tray from below and to agitate the mixture of liquid and solid esterification catalyst in a zone of turbulence on the tray and to keep the catalyst particles in suspension. In order to avoid the danger of "hot spots" forming on the tray through formation of pockets of settled catalyst particles, the floor of each tray is preferably designed so as to slope towards the zone of turbulence at an angle which exceeds the angle of repose of the catalyst particles under the liquid. Each esterification tray additionally has a downcomer means which permits liquid, but not catalyst particles, to flow down from that tray to the next lower one. The downcomer means will usually be provided with a screen to prevent catalyst particles passing downwardly therethrough.

One benefit of carrying out the reaction in a column reactor of this type is that the water produced in the reaction may be removed from the top of the column reactor in a vapour stream while ester products may be recovered from the sump of the reactor or from a tray located towards the bottom of the column. Thus, as the liquid flows down the trays it encounters progressively drier reaction conditions and the esterification reaction is therefore driven further towards 100% ester formation.

A liquid catalyst may be used in the present invention and where a liquid catalyst is selected, the or each reactor will be selected and modified accordingly.

Any suitable reaction conditions may be used in the or each reactor. Where a column reactor of the type described above is used temperature and pressure will be selected as those under which the alcohol distils. Such temperature and pressure conditions will vary depending on the alcohol selected but, where the alcohol is a $C_1$ to $C_4$ alcohol, will typically include use of a temperature of from about 65° C. to about 135° C. and a pressure of from about 1 bar to about 3 bar.

A typical solid esterification catalyst is the ion exchange resin sold under the trade name Amberlyst™ 16 by Rohn and Haas (U.K.) Limited of Lennig House, 2 Mason's Avenue, Croydon CR9 3NB, England or that available as DPT1 ion exchange resin from Davy Process Technology Limited of The Technology Centre, Princeton Drive, Thornaby, Stockton-on-Tees TS17 6PY, England. Suitable liquid catalysts include $H_2SO_4$ and p-toluenesulphonic acid.

The vapour phase stream emerging from the topmost esterification tray comprises alcohol vapour and water vapour; it may further include unconverted acid, and byproducts such as alkyl ether and traces of the alkyl ester. A further additional tray or trays may be provided above the uppermost esterification tray to act as a form of washing column in order to return alkyl ester to the esterification trays. These additional trays will usually be free of catalyst.

Alkyl esters of light acids such as acetic and acrylic acids which may be present in the maleic acid may be removed together with any alkyl ether from the esterification zone as a light overhead stream. Where a column reactor is used for the second stage of a two stage reaction, the ester will be recovered from the bottom of the column.

In a further aspect of the present invention, the ester recovered in step (d) is contacted with a hydrogen containing stream in a hydrogenation zone containing a charge of a hydrogenation catalyst effective for catalytic hydrogenation to convert at least some of the ester to a desired product. Thus the ester can then be subjected to hydrogenation by conventional means to provide the desired products. Examples of suitable hydrogenation processes can be found in U.S. Pat. No. 4,584,419, U.S. Pat. No. 4,751,334, WO-A-88/00937, WO99/25678, WO99/48852, WO97/43234, and WO97/43242 which are incorporated herein by reference. Where the ester is a di-($C_1$ to $C_4$ alkyl) maleate, a di-($C_1$ to $C_4$ alkyl) succinate or a $C_1$ to $C_4$ alkyl ester of 3-hydroxypropionic acid, the product of the hydrogenation reaction will be at least one of butane-1,4-diol, γ-butyrolactone and tetrahydrofuran which is recovered from the hydrogenation zone.

In this further aspect of the present invention, the water produced in the esterification step is preferably removed as far as possible prior to the ester being passed to the hydrogenation zone such that it is essentially dry ester which is passed to the hydrogenation zone. Thus, in a preferred embodiment of the present invention, it is essential dry di-($C_1$-$C_4$ alkyl) maleate which is passed to the hydrogenation zone.

Hydrogenation is advantageously carried out in the vapour phase in the presence of a heterogeneous ester hydrogenation catalyst. Typical hydrogenation catalysts include reduced promoted copper catalysts, for example reduced copper chromite catalysts such as that sold under the designation 85/1 by Davy Process Technology Limited of The Technology Centre, Princeton Drive, Thornaby, Stockton-on-Tees TS17 6PY, England.

Hydrogenation may be conducted at any suitable temperature and pressure but is preferably conducted at an elevated temperature of, for example, from about 150° C. to about 300° C. more preferably to about 240° C. and at a pressure of from about 5 bar to about 100 bar, preferably from about 50 bar to about 70 bar. In the preferred process, a product mixture of the $C_1$-$C_4$ alcohol, butane-1,4-diol, tetrahydrofuran, and γ-butyrolactone is produced. Even if the primary product of interest is the butane-1,4-diol, the presence of minor amounts of tetrahydrofuran and γ-butyrolactone is not disadvantageous since these are important chemicals of commerce and it is therefore economic to recover them in pure form. If desired, the γ-butyrolactone may be recycled to the hydrogenation zone to produce additional butane-1,4-diol.

In one arrangement of the present invention, the alcohol is recovered from the hydrogenation zone and recycled to the esterification zone of step (a).

The invention will now be described by way of example, with reference to the formation of a di-($C_1$ to $C_4$ alkyl) maleate and its subsequent hydrogenation to butane-1,4-diol, tetrahydrofuran, and γ-butyrolactone and with particular reference to the accompanying drawings in which:

FIG. 3 is a schematic representation of an alternative arrangement of the process in the esterification zone.

Figure 1:
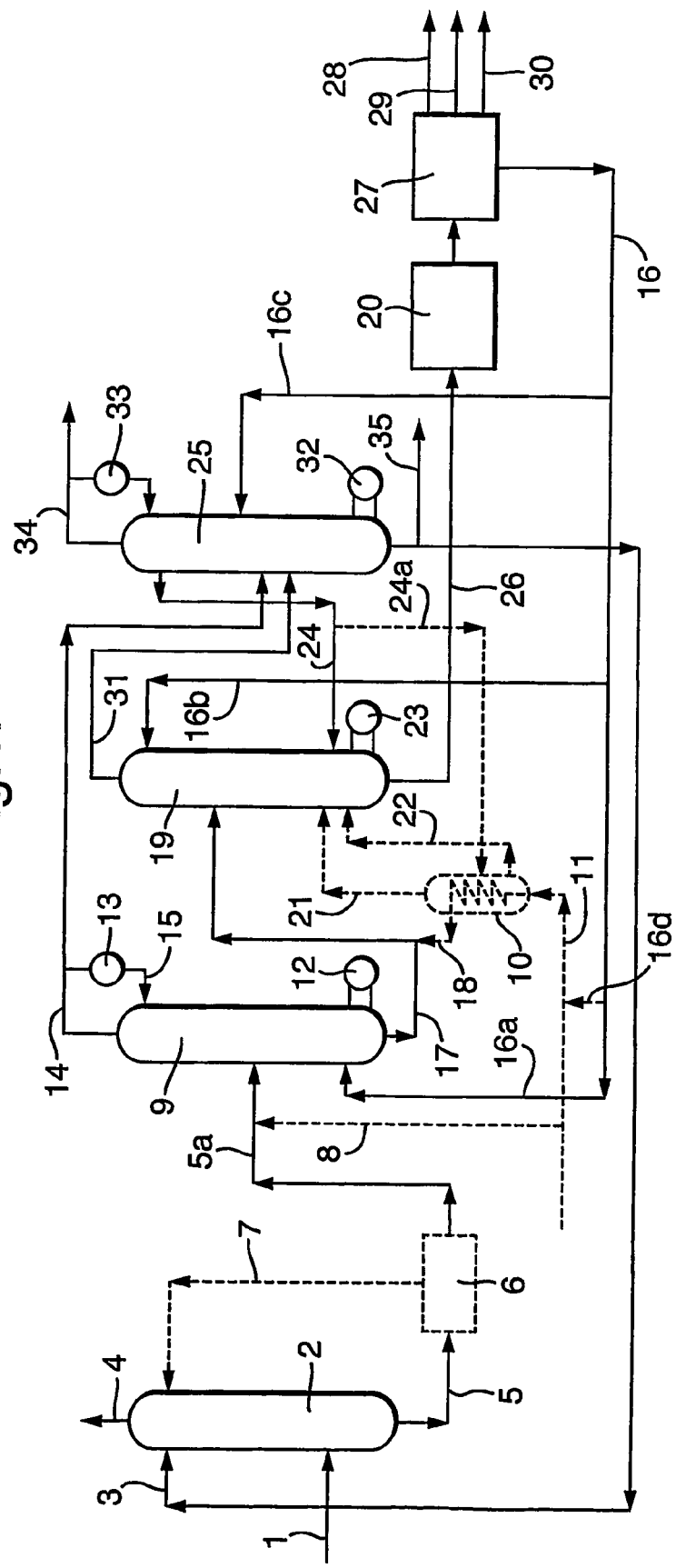
FIG. 1 is a schematic representation of a process in accordance with the present invention.

It will be understood that since the accompanying drawings are schematic, many other items of equipment which are not present in the drawings may be required in the plant. Such additional items include, but are not limited to, pumps, holding tanks, valves, pressure sensors, temperature sensors, pressure controllers, temperature controllers, level sensors, heaters, coolers, surge tanks, condensers, column reboilers and the like. Any such item of equipment would be installed in accordance with conventional engineering practice.

As illustrated in FIG. 1, the product of a maleic anhydride reactor, which is a hot stream including maleic anhydride, is passed via line 1 to an absorber 2 in which the hot stream is cooled and scrubbed by being contacted with water which also converts the maleic anhydride to maleic acid. Part of the maleic anhydride may be condensed out of the vapour stream by a partial condenser (located in line 1 but not shown).

In addition to any fresh water which may be added to the absorber though a water feed line (not shown) the main source of water for the absorber is that recycled from the esterification zone which is discussed in detail below. The recycled water is added to the absorber via line 3. Gases which will include oxygen, nitrogen, carbon dioxide and carbon monoxide saturated with water are vented from the absorber via vent line 4 and an aqueous solution of maleic acid is removed from the bottom of the absorber in line 5. The aqueous solution of maleic acid is optionally concentrated in zone 6 and the excess water resulting from the concentration of the aqueous solution is recycled to the absorber via line 7.

The aqueous solution, which may or may not have been concentrated, is then fed in line 5a to a reaction column 9 that may contain a catalyst located on trays. The maleic acid will then be reacted under suitable temperature and pressures with a $C_1$ to $C_4$ alkanol to form the mono-ester. For ease of reference the following discussion will refer to methanol. However, it will be understood that methanol may be replaced by any $C_2$ to $C_4$ alkanol. Suitable temperatures include from 65 to 150° C. and suitable pressures include from 1 to 5 bar.

A feed of maleic anhydride and/or crude maleic anhydride for example from the partial condenser is optionally fed to the mono-esterification reactor 9 via line 8 or alternatively may undergo separate mono-esterification in separate mono-ester reactor 10. The maleic anhydride and/or crude maleic anhydride is fed to the bottom of reactor 10 via line 11.

The reactor column 9 includes a reboiler 12 located at or near the bottom of the column and a condenser 13 is located in a suitable position to condense any unconverted maleic acid or heavies leaving the top of the column via line 14. The condensate is returned to the column 9 via line 15. Methanol may be fed directly to the reaction column by a feed line (not shown). The methanol will normally be at the bottom. However, the prime source of methanol is that recycled from later stages in the reaction process. Recycled methanol is fed to column 9 via line 16.

Following the reaction to form the mono-ester, bottoms comprising the mono ester, unreacted maleic acid and water are removed via line 17. The bottoms stream may additionally include any diester formed. This stream may be combined with mono-ester product from parallel reactor 10 which is removed from the reactor via line 18.

The mono-ester is then fed to the second reaction column 19 where it will be further reacted with methanol in the presence of a catalyst and at suitable temperatures and pressures. Suitable temperatures and pressures include those detailed in connection with the mono-esterification reaction.

Methanol may be fed directly to column 19 via a feed line (not shown) but is preferably provided at least in part by recycled methanol collected downstream and recycled via line 24. Additional methanol may also be recycled via the optional reactor 10. The methanol may be fed to the reactor 19 as vapour which is removed from the top of reactor 10 in line 21 and/or as a liquid in line 22. Methanol may also be added to the column (in line 16b) as a wash to reduce the maleate and maleic acid content of overhead stream, line 31. This additional methanol will preferably be added at or near the top of the column. This methanol, which may be recycled methanol recovered downstream in the process, is fed to the reactor 19 via line 16b.

The reaction column 19 will preferably include a reboiler 23 located at or near the bottom of the column.

In column 19, the mono-ester is reacted with the methanol to form the dimethyl maleate product. This product will be removed from the bottom of the column via line 26 and transferred to a hydrogenation zone 20 in which the dimethyl maleate will be contacted with hydrogen in the presence of a suitable catalyst and at suitable reaction conditions to form the products including butane-1,4-diol and/or tetrahydrofuran and/or γ-butyrolactone. A particular feature of the present invention is that the process used for forming the ester does not impinge on the reaction conditions required for the subsequent hydrogenation reaction and thus any of the conventional catalysts and process conditions can be used.

A product stream is taken from the hydrogenation zone 20 to a refining zone 27 where the products are separated and removed via lines 28, 29 and 30. Methanol recovered in the refining zone 27 is removed via line 16 and may be recycled to one or more of: the mono-esterification reactor column 9 via line 16a; the reaction column 19 via line 16b and the methanol column 25 via line 16c. Where the optional reactor 10 is present, a proportion of the methanol may be additionally or alternatively recycled via line 16d to the reactor 10.

The lights from reactor column 19 which comprise predominantly methanol and water with any di-alkylether and alkyl ester of light acids such as acetic or acrylic acid together with small amounts of di-methyl maleate and small amounts of maleic acid are removed from the top of the column and passed via line 31 to the methanol column 25 in which the methanol and water are separated. The column may include a reboiler 32 and a condenser 33. Methanol recovered from the column may be recycled as feed to reactor 19 via line 24. Where the optional reactor 10 is present, a portion of the methanol may be recycled to the reactor via line 24a.

Lights exit from the top of the methanol column 25 via line 34 and some may be vented to fuel while the remainder is condensed in condenser 33 and returned to the top of the column. The column bottoms which will predominantly comprise water and recovered maleic acid and di-methyl maleate, will be recycled via line 3 to the absorber 2. A portion of the water may be purged via line 35.

Figure 2:
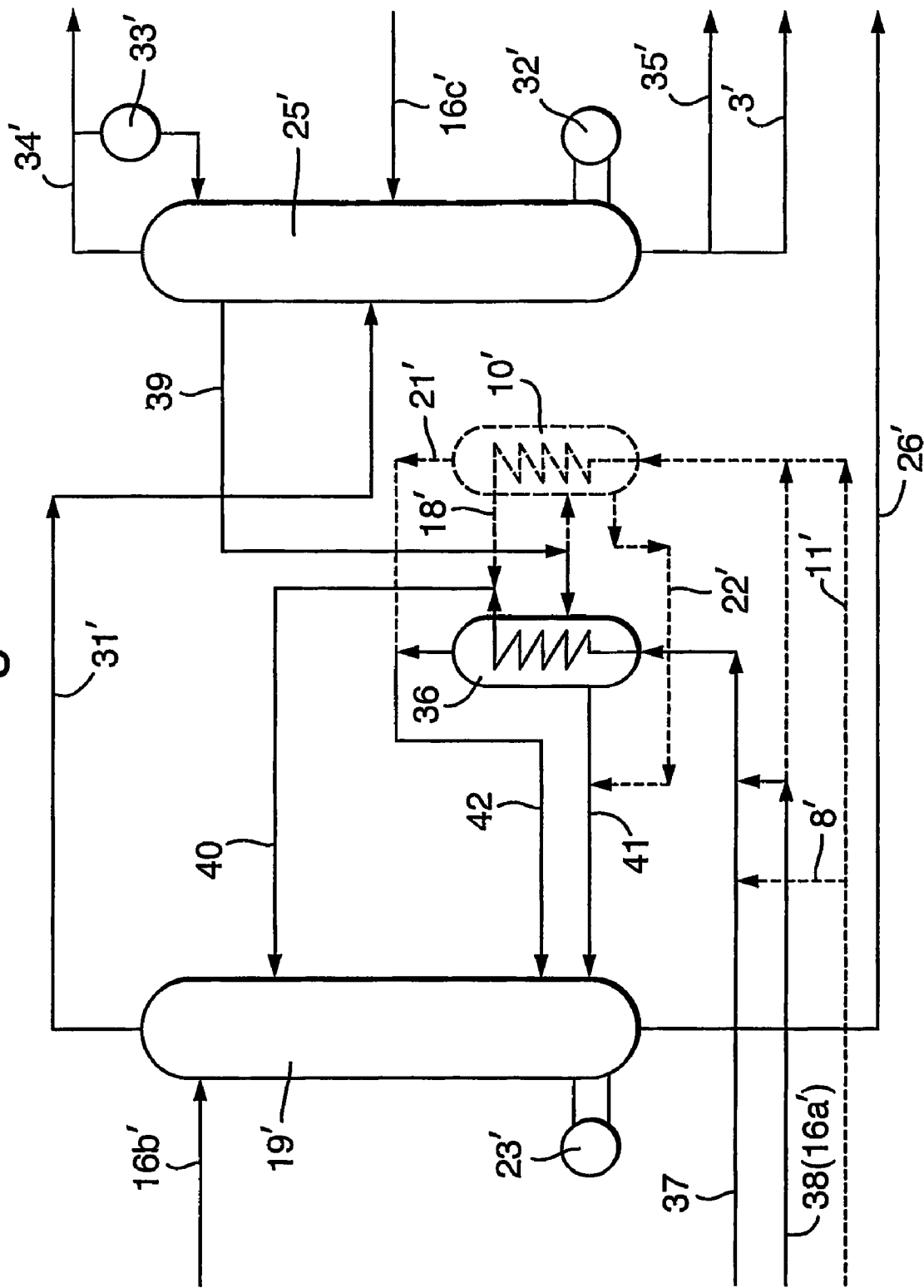
FIG. 2 is a schematic representation of one arrangement of the process in the esterification zone.

FIG. 2 represents a modification of a part of the process illustrated in FIG. 1. For convenience, corresponding parts of the system will be designated by the same numeral as in FIG. 1 but with the indica'. Elements of the process which are different from those in FIG. 1 have been given different numerals even if they provide the same function.

In this modified arrangement, the mono-esterification reaction column of FIG. 1 is replaced with a plug flow reactor 36 which has a residence time of from about 3 minutes to about 20 minutes. In this process, the aqueous maleic acid solution from the absorber 2 of FIG. 1 is fed to the plug flow reactor 36 via line 37. This may optionally be mixed with recycled methanol from line 38 (which corresponds to line 16a in Scheme 1). The plug flow reactor will also be fed with methanol from the methanol column 25' in line 39. The resulting monomethyl maleate is removed from the reactor 36 via line 40 and fed to the reaction column 19' in which the dimethyl maleate will be formed. Methanol liquid will be recovered from the reactor 36 and recycled to the reaction column 19' in line 41 and methanol vapour will be recycled to the reaction column 19' in line 42.

As in the process of FIG. 1, a feed of maleic anhydride and/or crude maleic anhydride may optionally be fed to the plug flow reactor 36 via line 8' or alternatively may undergo separate mono-esterification in parallel to the mono-esterification in plug flow reactor 10' via line 11'. The plug flow reactor 10' or 36 may be separate units or may be located within a containment vessel with the mono-esterification reactor.

Methanol vapour from reactor 10' will exit via line 21' and will be added to the vapour from reactor 36 in line 42. Methanol liquid from reactor 10' will exit via line 22' and will be added to the liquid from reactor 36 in line 41. The monomethylmaleate will be removed from the reactor via line 18' where it is mixed with the monomethylmaleate from reactor 36 which is fed via line 40 to the top of reactor column 19'.

The monomethyl maleate fed into the reactor column 19' is reacted with further methanol to form the dimethyl maleate. The reactor preferably includes a heater 23' which serves to drive the methanol up the reactor column. Recycled methanol from the downstream hydrogenation zone is fed to the reaction column 19' via line 16b'. The dimethyl maleate is removed from the bottom of reactor 19' via line 26' from which it is fed to hydrogenation zone 20.

Methanol containing water and small amounts of maleic acid and di-methyl maleate, is removed from the top of the column 19' in line 31' and is fed to the methanol column 25' in which the water and methanol are separated. The column may include a reboiler 32' and a condenser 33'. Methanol recovered is recycled to the first esterification reactor 36 via line 39. Methanol recovered in the post-hydrogenation refining zone is fed to reactor 36 and also optionally to 10' in line 38.

As in the scheme of FIG. 1, column lights exiting form the top of column 25' via line 34' may be vented to fuel or may be condensed in condenser 33' and returned to the top of the column. The column bottoms which will predominantly comprise water and recovered maleic acid and di-methyl maleate, will be recycled via line 3' to the absorber 2 (illustrated in FIG. 1). A portion may be purged via line 35'.

In this process, if a 95 wt % maleic acid feed is used, about 70 to 80% of the maleic acid will be esterified to the mono-ester in the plug flow reactor and about 4.4 mols of non-reaction methanol (i.e. a total of 5.4 mols of methanol) are required to strip the water for each mole of maleic acid in the feed.

The alternative process of FIG. 3 is similar to that of FIG. 2. However, a heater 43 is incorporated close to the feed point of the reaction column. Whilst the heater is illustrated as being an external heater, it will be understood that it may be located within the reaction column. Where the heater is an external heater, it may act to heat the feed and/or heat and vaporise a recycle from the column. This heater provides heat to boil off the water in the feed near to the top of the column. This allows that the water concentration on the reaction stages below the feed and the temperature profile are similar to that which would be attained using a maleic anhydride feed. Thus with a 95 wt % maleic acid feed, about 2.5 mols of non-reaction methanol (i.e. a total of about 3.5 mols) are required to strip out the water in the reaction column for each mole of maleic anhydride in the feed.

Whilst the schemes of FIGS. 2 and 3 provide acceptable results, the Scheme of FIG. 1 in which an autocatalytic mono-ester reaction column (MERC) is used in place of the plug flow reactor, enables more dilute streams of maleic acid solution to be processed efficiently. Without wishing to be bound by any theory, the principle of this scheme is to feed the aqueous solution of maleic acid to a column in which a suitable residence time is provided to convert the maleic acid to the mono-ester and the reaction/feed water is driven off at least in part by the energy provided by the enthalpy of reaction. In a particularly preferred arrangement, no catalyst is required in this column.

Distillation trays and a condenser/reflux system are preferably provided above the MERC feed point such that losses of the maleic acid species in overheads are minimised. Any loss of maleic acid species will be recovered in the methanol column and recycled to the absorber.

Greater than 80% conversion of the maleic acid feed is obtained by this preferred process with a 95 wt % maleic acid feed and the water fed to the diester reaction column is reduced to less than 10 mol %. For a 95 wt % maleic acid feed the overall methanol requirement in the second reaction column is reduced to about 2 to about 5, preferably about 3 mol/mole of maleic acid ie to similar to that required for a maleic anhydride feed.

The scheme of FIG. 1 is particularly suitable for use with more dilute feed of maleic acid as the MERC is particularly suitable for separating out additional water prior to the mono-ester being passed to the di-ester reaction column. In this preferred scheme, equipment normally used to concentrate the maleic acid feed may be eliminated thereby reducing costs.

A catalyst may not be required for the mono-esterification but where one is used, a solid or liquid catalyst may be employed. A catalyst will normally be required in the reaction column used to convert the mono-ester to the di-ester and again this may be a solid or a liquid catalyst. In a particularly preferred arrangement, a solid catalyst is used throughout the esterification zone.

The present invention will now be described with reference to the following examples.

COMPARATIVE EXAMPLE 1

A butane oxidation reactor produces 100 moles per hour of maleic anhydride, of which 40 kmols are condensed by cooling the gases in condensers. The remaining 60 moles per hour are recovered as a 50 wt % aqueous solution of maleic acid from an absorber. This is fed to an evaporation system to concentrate the solution of maleic acid. The concentrated solution is fed to a dehydration reactor system to produce a stream of crude maleic anhydride. This maleic anhydride, together with the crude maleic anhydride from the partial condensers is fed to an esterification unit. The crude maleic acid is mixed with recycle methanol from the refining section and fed to a plug flow, mono-ester reactor. The product from this is fed to a reaction column to react the mono-methyl maleate with methanol to produce di-methyl maleate. 300 mols per hour of methanol are fed to the bottom of the reaction column. Essentially dry, fully converted di-methyl maleate is fed to hydrogenation. Recycle methanol from the refining section is fed to the top of the reaction column as washed to minimise the di-methyl maleate in the overhead of the column.

Methanol and water from the overhead of the reaction column is fed to the methanol column where the methanol is separated and recycled to the reaction column.

EXAMPLE 1

This example is particularly relevant to the arrangement of FIG. 2. A butane oxidation reactor (not shown) produces 100 moles per hour of maleic anhydride, of which 40 kmols are condensed by cooling the gases in condensers (not shown). The remaining 60 moles per hour are recovered as a 50 wt % aqueous solution of maleic acid from an absorber (2) in line (5). This is fed to an evaporator system (6) and the maleic acid is concentrated (line 5a/37) and mixed together with the crude maleic anhydride from the partial condensers (line 8') to form a 95 wt % solution of maleic acid. The aqueous maleic acid feed is mixed with recycled methanol from the refining section (line 38/16a') and fed to a plug flow, mono-ester reactor (36), where more than 80% of the maleic acid is converted to mono-methyl maleate. The product from this is fed to a reaction column (19') to react the mono-methyl maleate with methanol to produce di-methyl maleate. 540 mols per hour of methanol (lines 42 and 41) are fed to the bottom of the reaction column (19'). Di-methyl maleate (line 26') is fed to hydrogenation (20). Recycle methanol from the refining section is fed to the top of the reaction column as wash (line 16b') to minimise the di-methyl maleate and maleic acid in the overhead of the column. Methanol and water from the overhead (line 31') of the reaction column is fed to the methanol column (25') where the methanol is separated and recycled to the reaction column (line 39). Water and a small amount of recovered maleic acid and di-methyl maleate from the bottom of the methanol column are recycled to absorber (2) in line 3'.

Thus this example clearly illustrates that the esterification can be carried out using a carboxylic acid starting material in the presence of water of solution that is additional to the water of esterification.

EXAMPLE 2

This example relates particularly to FIG. 3 and illustrates use of a side heater in the reaction column. In this example a 95 wt % solution of aqueous maleic acid is provided as described in Example 1. The aqueous maleic acid feed is mixed with recycle methanol from the refining section (line 38/16a') and fed to a plug flow, mono-ester reactor (36), where more than 80% of the maleic acid is converted to mono-methyl maleate. The product from this is fed to reaction column (19') to react the mono-methyl maleate with methanol to produce di-methyl maleate. This reaction column includes a heater near the feed point. The heater helps to drive off water from the column. 350 moles per hour of methanol (lines 42 and 41) are fed to the bottom of the reaction column (19'). Essentially water free, fully converted di-methyl maleate (line 26') is fed to hydrogenation (20). Recycle methanol from the refining section is fed to the top of the reaction column as wash (line 16b') to minimize the di-methyl maleate and maleic acid in the overhead of the column. Methanol or water from the overhead (line 31') of the reaction column is fed to the methanol column (25') where the methanol is separated and recycled to the reaction column (line 39). Water and a small amount of recovered maleic acid and di-methyl maleate from the bottom of the methanol column are recycled to the absorber (2) in line 3'.

EXAMPLE 3

This example relates to FIG. 1. In this example a 95 wt % solution of aqueous maleic acid is provided as described in Example 1. The aqueous maleic acid is fed to the mono-ester reactor column (9). Recycled methanol from the refining section (line 16a) is fed to the bottom of the column 9. More than 80% of the maleic acid is converted to mono-methyl maleate from the bottom product line (line 17) contains less than 10 mole % water. Mainly water and methanol and a small amount of maleic acid in the overhead (line 14) are fed to the methanol column (line 25). The bottom product from column (9) is fed to a reaction column (19) to react the mono-methyl maleate with methanol to produce di-methyl maleate. 300 mols per hour of methanol (line 24) are fed to the bottom of the reaction column (19). Essentially water free, fully converted di-methyl maleate is fed (line 26) to hydrogenation in reactor (20). Recycle methanol from the refining section is fed to the top of the reaction column as wash (line 16b) to minimise the di-methyl maleate and maleic acid in the overhead of the column. Methanol and water from the overhead (line 31) of the reaction column is fed to the methanol column (25) where the methanol is separated and recycled to the reaction column (line 24). Water and a small amount of recovered maleic acid and di-methyl maleate from the bottom of the methanol column are recycled to the absorber (2) in line 3.

EXAMPLE 4

This example also refers to FIG. 1. A butane oxidation reactor (not shown) produces 100 moles per hour of maleic anhydride, of which 40 kmols are condensed by cooling the gases in condensers (not shown). The remaining 60 moles per hour are recovered as a 50 wt % aqueous solution of maleic acid from an absorber (2) in line 5 and mixed together with the crude maleic anhydride from the partial condensers (line 8). The aqueous maleic acid is fed to the mono-ester reaction column (9). Recycle methanol from the refining section is fed (line 16a) to the bottom of the column (9). More than 80% of the maleic acid is converted to mono-methyl maleate and the bottom product (line 17) contains less than 20 mol % water. Mainly water and methanol and a small amount of maleic acid in the overhead are fed (line 14) to the methanol column (25). The bottom product from the mono-ester reaction column (9) is fed to a reaction column (19) to react the mono-methyl maleate with methanol to produce di-methyl maleate. 300 moles per hour of methanol are fed (line 24) to the bottom of the reaction column (19). Essentially water free, fully converted di-methyl maleate is fed (line 26) to hydrogenation. Recycle methanol from the refining section is fed to the top of the reaction column as wash (line 16b) to minimise the di-methyl maleate and maleic acid in the overhead of the column. Methanol and water from the overhead (line 31) of the reaction column is fed to the methanol column (25) where the methanol is separated and recycled to the reaction column (line 24). Water and a small amount of recovered maleic acid and di-methyl maleate from the bottom of the methanol column are recycled to the absorber (2) in line 3. Thus in this arrangement the evaporator and the mono-ester reaction column duties are combined in a single unit which will reduce the equipment costs by eliminating the evaporation equipment.

Relative heat duties compared to a total of 100 for Comparative Example 1 are set out in Table I.

TABLE I

| | Comparative Example 1 | Example 1 | Example 2 | Example 3 | Example 4 |
|---|---|---|---|---|---|
| Evaporation System | 40 | 31 | 31 | 31 | — |
| Dehydration System | 16 | — | — | — | — |
| Mono-ester Reaction Column | — | — | — | 18 | 33 |
| Reaction Column | 27 | 56 | 42 | 26 | 26 |
| Methanol Column | 17 | 28 | 23 | 21 | 28 |
| Total | 100 | 115 | 96 | 96 | 89 |

Thus these examples illustrate not only that the reaction can be carried out in the presence of water but also that in some preferred arrangement the heat requirements are lower than are noted in conventional systems.

The invention claimed is:

1. A process for the diesterification of maleic acid by reaction of maleic acid with methanol in the presence of water of solution comprising the steps of:
    (a) providing a feed solution comprising maleic acid and the water of solution;
    (b) reacting the feed solution comprising maleic acid in an esterification zone with methanol to form dimethyl maleate and water of esterification; said esterification being conducted at temperatures of from 65 to 150° C. and pressures from 1 to 5 bar in a two-stage process;
    (c) removing the water of solution and the water of esterification; and
    (d) recovering the dimethyl maleate.

2. A process according to claim 1 wherein the process is a continuous process.

3. A process according to claim 1 wherein the water removed in step (c) is recycled to step (a).

4. A process according to claim 1 wherein the feed solution in step (a) comprises from about 50 to about 70 wt% water.

5. A process according to claim 1 wherein the feed solution is processed prior to its supply to step (a) to reduce the water content.

6. A process according to claim 1 in which the feed solution comprising maleic acid is subjected in the first stage to mono-esterification in parallel with a mono-esterification of a feed of anhydride.

7. A process according to claim 1 in which the reaction of step (b) is carried out in an esterification zone comprising a first reactor in which maleic acid is converted to the mono ester and a second reactor in which the mono ester is converted to the diester.

8. A process according to claim 1 in which one or more heaters is provided in the esterification zone, wherein the esterification zone comprises one or more reactors.

9. A process according to claim 8 in which at least one heater is located close to the feed point of at least one reactor.

10. A process according to claim 1 in which the water of solution and the water of esterification are substantially stripped out.

11. A process according to claim 1 in which the esterification is carried out in the presence of a catalyst.

12. A process according to claim 1 in which the second stage step of the esterification reaction is carried out in the presence of a catalyst.

13. A process according to claim 11 in which the catalyst is a liquid catalyst.

14. A process according to claim 1 wherein the dimethyl maleate recovered in step (d) is contacted with a hydrogen containing stream in a hydrogenation zone containing a charge of a hydrogenation catalyst effective for catalytic hydrogenation to convert at least some of the dimethyl maleate to a desired product.

15. A process according to claim 14 wherein the water of solution and the water of esterification is removed prior to the dimethyl maleate being passed to the hydrogenation zone.

16. A process according to claim 14 wherein hydrogenation is carried out in the vapour phase in the presence of a heterogeneous ester hydrogenation catalyst.

17. A process according to claim 14 wherein methanol is recovered from the hydrogenation zone and recycled to the esterification zone of step (b).

18. A process according to claim 1 in which the feed solution comprising maleic acid to be formed by hydrolysis of the product from a maleic anhydride reactor and a water rich stream recovered from the esterification zone is recycled to an absorber in which hydrolysis of the product from the maleic anhydride reactor is carried out.

19. A process according to claim 12 in which the catalyst is a liquid catalyst.

* * * * *